United States Patent
Ramos et al.

(10) Patent No.: US 11,157,936 B2
(45) Date of Patent: Oct. 26, 2021

(54) PRODUCT DISCOVERY VIA CONNECTED KITCHEN

(71) Applicant: International Business Machines Corporation, Armonk, NY (US)

(72) Inventors: Igor S. Ramos, Round Rock, TX (US); Anindita Das, Austin, TX (US); Ohannes Ohannessian, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/785,592

(22) Filed: Feb. 8, 2020

(65) Prior Publication Data
US 2021/0248637 A1    Aug. 12, 2021

(51) Int. Cl.
*G06Q 30/00* (2012.01)
*G06Q 30/02* (2012.01)
(Continued)

(52) U.S. Cl.
CPC ..... *G06Q 30/0224* (2013.01); *G06K 9/00664* (2013.01); *G06K 9/6267* (2013.01);
(Continued)

(58) Field of Classification Search
CPC ........... G06Q 30/0224; G06K 9/00664; G06K 9/6267
See application file for complete search history.

(56) References Cited

U.S. PATENT DOCUMENTS 8,538,829 B1 * 9/2013 Hu .............. G06Q 30/0281
705/26.1
9,965,798 B1 * 5/2018 Vaananen ........... F25D 27/005
(Continued)

FOREIGN PATENT DOCUMENTS

WO    2016206889 A1    12/2016

OTHER PUBLICATIONS

Lee, Nicole, "Amazon's Alexa-powered microwave is pretty unnecessary" [online], Engadget, retrieved on Nov. 20, 2019 from the Internet URL: https://www.engadget.com/2018/09/20/amazonalexamicrowavehandson/ (2019).
(Continued)

*Primary Examiner* — Scott C Anderson
(74) *Attorney, Agent, or Firm* — William H. Hartwell

(57) ABSTRACT

Product discovery is enhanced by allowing a user in a connected kitchen to share their food consumption habits with friends and trusted companies. Smart devices installed in the kitchen sense the food being prepared, such as a camera which automatically records an image of a food item, and image recognition is performed to identify the item. A cloud server has contact information for individuals associated with the user such as designated friends or social groups, and also has promotional information for available sales offers regarding food-related products. The server generates a food product recommendation based on the dish being prepared by the user and based on the sales offers, and sends a notification to the friends identifying the user, the dish and a particular sales offer. The system rewards users based on their influence, gleaned from the number of such offers that are accepted by the friends.

20 Claims, 7 Drawing Sheets

(51) Int. Cl.
*G06Q 50/12* (2012.01)
*G06Q 50/00* (2012.01)
*G06K 9/62* (2006.01)
*G06K 9/00* (2006.01)
*G16H 20/60* (2018.01)

(52) U.S. Cl.
CPC ............. *G06Q 50/01* (2013.01); *G06Q 50/12* (2013.01); *G06K 2209/17* (2013.01); *G16H 20/60* (2018.01)

(56) References Cited

U.S. PATENT DOCUMENTS

| | | | |
|---|---|---|---|
| 2011/0119130 A1 | 5/2011 | Agan et al. | |
| 2015/0106183 A1* | 4/2015 | McEvilly | H04W 4/025 705/14.25 |
| 2015/0248651 A1 | 9/2015 | Akutagawa | |
| 2016/0327281 A1 | 11/2016 | Bhogal | |
| 2016/0335588 A1* | 11/2016 | Knobel | G06F 16/23 |
| 2018/0197135 A1* | 7/2018 | Moyer | G06Q 50/10 |
| 2018/0268431 A1* | 9/2018 | Harris | G06N 3/084 |
| 2018/0308143 A1 | 10/2018 | Chan et al. | |
| 2019/0147522 A1 | 5/2019 | Susser et al. | |
| 2020/0098466 A1* | 3/2020 | Murdoch | H04W 4/021 |
| 2020/0226659 A1* | 7/2020 | Shimoirisa | G06Q 30/0631 |

OTHER PUBLICATIONS

Heater, Brian, "Is a $600 smart oven ever worth it?" [online], TechCrunch, retrieved on Nov. 20, 2019 from the Internet URL: https://techcrunch.com/2019/05/19/isa600smartoveneverworthit/ (2019).

Griffiths, Sarah, "The 'microwave' that counts CALORIES: Device uses waves travelling through food to calculate its nutritional value" [online], Daily Mail, retrieved on Nov. 20, 2019 from the Internet URL: https://www.dailymail.co.uk/sciencetech/article2684476/ThemicrowavecountsCALORIESDeviceuseswavestravellingfoodcalculatenutritionalvalue.html (2014).

* cited by examiner

PRODUCT DISCOVERY VIA CONNECTED KITCHEN

BACKGROUND OF THE INVENTION

Field of the Invention

The present invention generally relates to food consumption, and more particularly to a method of discovering and sharing food preparation ideas.

Description of the Related Art

Computer systems are continually becoming more involved with day-to-day human activities. One area in particular where this has occurred is food consumption. A variety of techniques have been devised to simplify food-related tasks from the start of the process to the end, e.g., grocery shopping, recipe generation, meal planning, food preparation, delivery, and service such as in restaurants. For example, U.S. Patent Application Pub. no. 2019/0147522 discloses a grocery preparation and fulfillment service management system which uses a search engine to retrieve ingredient availability data and create purchase orders based on recipes of dishes and the ingredient availability. Purchase order creation can be supported by voice recognition services such as using a virtual assistant which allows a user to easily obtain necessary ingredients for a particular recipe. The system described in U.S. Patent Application Pub. no. 2011/0119130 allows customized meal planning based on a user's social network interactions and a personal food profile. In U.S. Patent Application Pub. no. 2018/0308143, a user can take photographs of food items, and food image recognition is used to automatically identify dishes present in the photos. This identification in turn can be used to populate a food and recipe database, suggest restaurants serving similar food, estimate nutritional content, or create a shopping list. Patent Cooperation Treaty Pub. no. WO 2016/206889 shows a related idea of using image recognition to determine a recipe for a food product produced by an individual.

Another trend affecting personal food consumption is the advent of smart homes which offer a variety of devices designed to enhance home living. A related idea is the smart kitchen which can have various appliances that are "connected", i.e., have wired or wireless communications with other devices or a larger network. These appliances make food preparation and serving easier and faster. While referred to as "smart", they mostly offer basic functionalities such as providing voice command for a microwave or conventional oven. Some appliances can be controlled remotely using a personal computing device such as a cell phone having an appropriately programmed application ("app"). These devices are directed to food preparation but there are also a variety of devices that have been designed for adjunct purposes such as determining nutritional information. For example, a prototype device by General Electric Global Research uses microwaves to count calories in a dish or meal.

SUMMARY OF THE INVENTION

The present invention in at least one embodiment is generally directed to a method of enhancing discovery of food products by receiving food preparation information from smart devices of a user in a connected kitchen, determining a dish likely being prepared in the kitchen based on the food preparation information, receiving contact information pertaining an individual associated with the user such as a friend on a social network, receiving promotional information for available sales offers regarding food-related products, and generating a food product recommendation based on the likely dish and one of the sales offers. A notification is then sent from a cloud server to the individual using the contact information, the notification identifying the user, the dish and the particular available sales offer. The cloud server can determine an optimal time to send the notification. The client devices can include a camera that records an image of the food item, and image recognition is performed on the image to identify the food item. The determination of the dish can be facilitated by a food profile of the user which has a history of their food consumption habits. In an illustrative implementation, the individual receiving the notification also has a food profile with dietary preferences, and the food product recommendation is based in part on those preferences. The system can allow marketers to reward users based on their influence, gleaned from the number of such offers that are accepted by the friends.

The above as well as additional objectives, features, and advantages in the various embodiments of the present invention will become apparent in the following detailed written description.

BRIEF DESCRIPTION OF THE DRAWINGS

The present invention may be better understood, and its numerous objects, features, and advantages of its various embodiments made apparent to those skilled in the art by referencing the accompanying drawings.

The use of the same reference symbols in different drawings indicates similar or identical items.

DESCRIPTION OF THE PREFERRED EMBODIMENT(S)

It is known that word-of-mouth is a great way for people to learn about products. For example, if someone learns that their friend Joe, who is a great cook, just prepared burgers he bought from a local grocery store and he found their taste awesome then the chances are, next time that person is buying burgers, they will follow Joe's lead and buy that same product. Also, Joe would probably welcome a product suggestion coming from this person, the local grocery store, or the burger company, after learning about his love for burgers.

The problem is that even though Joe is willing to share his food habits, and take suggestions for similar products, it is a very cumbersome process for him to do the sharing on a regular basis. The current process requires him to take a picture of the food, do a write-up about its qualities, such as thickness, time to cook, where he purchased it, etc., and then send all that information to friends or groups on social media platforms or via other electronic communications. It would accordingly be desirable to devise an improved method of creating a seamless mechanism for users to share their food habits with friends and companies they trust. It would be further advantageous if the method could provide opportunities for further product discoveries and offer tailored marketing based on those discoveries.

The present invention in its sundry implementations facilitates these and other advantages by enhancing product discovery (a consumer learning about a new product or reengaging) using home or kitchen installed devices that can automatically identify the food being prepared and served and then, with the user's consent, share that information with their social network, friends and companies they trust. With that integration, the present invention can allow tailored product offerings to the user and their friends, particularly based on their food consumption habits which can be determined by using this system as well other known external preference sources.

Various aspects of the present invention may be practiced using an assortment of computing devices such as traditional computers, smartphones, or cloud computing services and each of these types of computing devices are described in detail below. However, those skilled in the art will appreciate that these devices are exemplary and the present invention may be practiced on other hardware or software platforms as technology advances permit.

Figure 1:
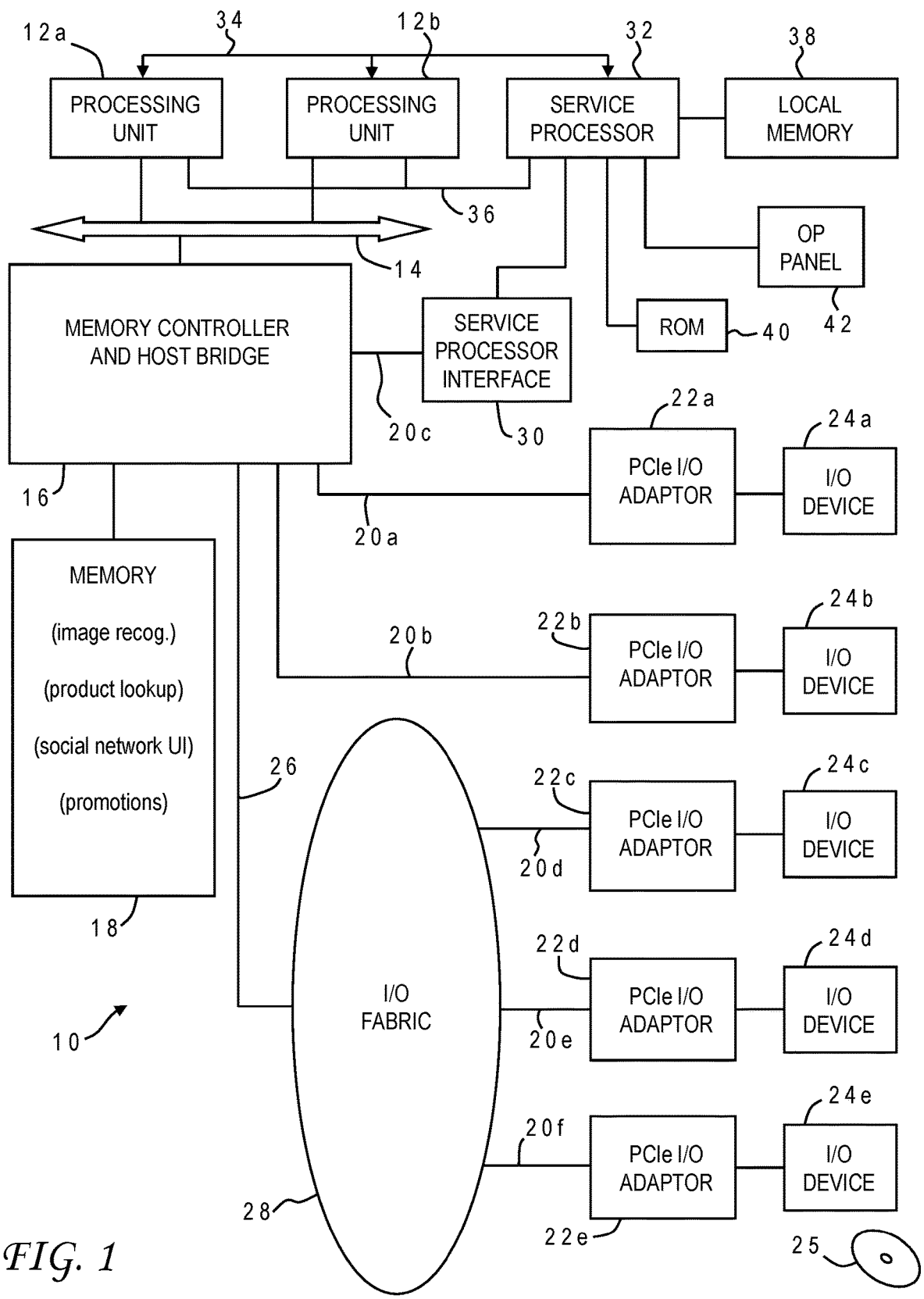
FIG. 1 is a block diagram of a computer system programmed to carry out food product discovery and sharing in accordance with one implementation of the present invention.

With reference now to the figures, and in particular with reference to FIG. 1, there is depicted one embodiment 10 of a computer system in which certain aspects of the present invention may be implemented to carry out product discovery and sharing. Computer system 10 is a symmetric multiprocessor (SMP) system having a plurality of processors 12a, 12b connected to a system bus 14. System bus 14 is further connected to and communicates with a combined memory controller/host bridge (MC/HB) 16 which provides an interface to system memory 18. System memory 18 may be a local memory device or alternatively may include a plurality of distributed memory devices, preferably dynamic random-access memory (DRAM). There may be additional structures in the memory hierarchy which are not depicted, such as on-board (L1) and second-level (L2) or third-level (L3) caches. System memory 18 has loaded therein one or more program applications in accordance with the present invention, such as image recognition, product lookup, social network user interfaces, and/or marketing promotions.

MC/HB 16 also has an interface to peripheral component interconnect (PCI) Express links 20a, 20b, 20c. Each PCI Express (PCIe) link 20a, 20b is connected to a respective PCIe adaptor 22a, 22b, and each PCIe adaptor 22a, 22b is connected to a respective input/output (I/O) device 24a, 24b. MC/HB 16 may additionally have an interface to an I/O bus 26 which is connected to a switch (I/O fabric) 28. Switch 28 provides a fan-out for the I/O bus to a plurality of PCI links 20d, 20e, 20f These PCI links are connected to more PCIe adaptors 22c, 22d, 22e which in turn support more I/O devices 24c, 24d, 24e. The I/O devices may include, without limitation, a keyboard, a graphical pointing device (mouse), a microphone, a display device, speakers, a permanent storage device (hard disk drive) or an array of such storage devices, an optical disk drive which receives an optical disk 25 (one example of a computer readable storage medium) such as a CD or DVD, and a network card. Each PCIe adaptor provides an interface between the PCI link and the respective I/O device. MC/HB 16 provides a low latency path through which processors 12a, 12b may access PCI devices mapped anywhere within bus memory or I/O address spaces. MC/HB 16 further provides a high bandwidth path to allow the PCI devices to access memory 18. Switch 28 may provide peer-to-peer communications between different endpoints and this data traffic does not need to be forwarded to MC/HB 16 if it does not involve cache-coherent memory transfers. Switch 28 is shown as a separate logical component but it could be integrated into MC/HB 16.

In this embodiment, PCI link 20c connects MC/HB 16 to a service processor interface 30 to allow communications between I/O device 24a and a service processor 32. Service processor 32 is connected to processors 12a, 12b via a JTAG interface 34, and uses an attention line 36 which interrupts the operation of processors 12a, 12b. Service processor 32 may have its own local memory 38, and is connected to read-only memory (ROM) 40 which stores various program instructions for system startup. Service processor 32 may also have access to a hardware operator panel 42 to provide system status and diagnostic information.

In alternative embodiments computer system 10 may include modifications of these hardware components or their interconnections, or additional components, so the depicted example should not be construed as implying any architectural limitations with respect to the present invention. The invention may further be implemented in an equivalent cloud computing network.

When computer system 10 is initially powered up, service processor 32 uses JTAG interface 34 to interrogate the system (host) processors 12a, 12b and MC/HB 16. After completing the interrogation, service processor 32 acquires an inventory and topology for computer system 10. Service processor 32 then executes various tests such as built-in-self-tests (BISTs), basic assurance tests (BATs), and memory tests on the components of computer system 10. Any error information for failures detected during the testing is reported by service processor 32 to operator panel 42. If a valid configuration of system resources is still possible after taking out any components found to be faulty during the testing then computer system 10 is allowed to proceed. Executable code is loaded into memory 18 and service processor 32 releases host processors 12a, 12b for execution of the program code, e.g., an operating system (OS) which is used to launch applications and in particular the product discovery programs of the present invention, results of which may be stored in a hard disk drive of the system (an I/O device 24). While host processors 12a, 12b are executing program code, service processor 32 may enter a mode of monitoring and reporting any operating parameters or errors, such as the cooling fan speed and operation, thermal sensors, power supply regulators, and recoverable and non-recoverable errors reported by any of processors 12a, 12b, memory

18, and MC/HB 16. Service processor 32 may take further action based on the type of errors or defined thresholds.

The present invention may be a system, a method, and/or a computer program product. The computer program product may include one or more computer readable storage media collectively having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Computer system 10 carries out program instructions for a product discovery process that uses novel techniques to share information and opportunities relating to food.

Accordingly, a program embodying the invention may additionally include conventional aspects of various social networking and marketing tools, and these details will become apparent to those skilled in the art upon reference to this disclosure.

Figure 2:
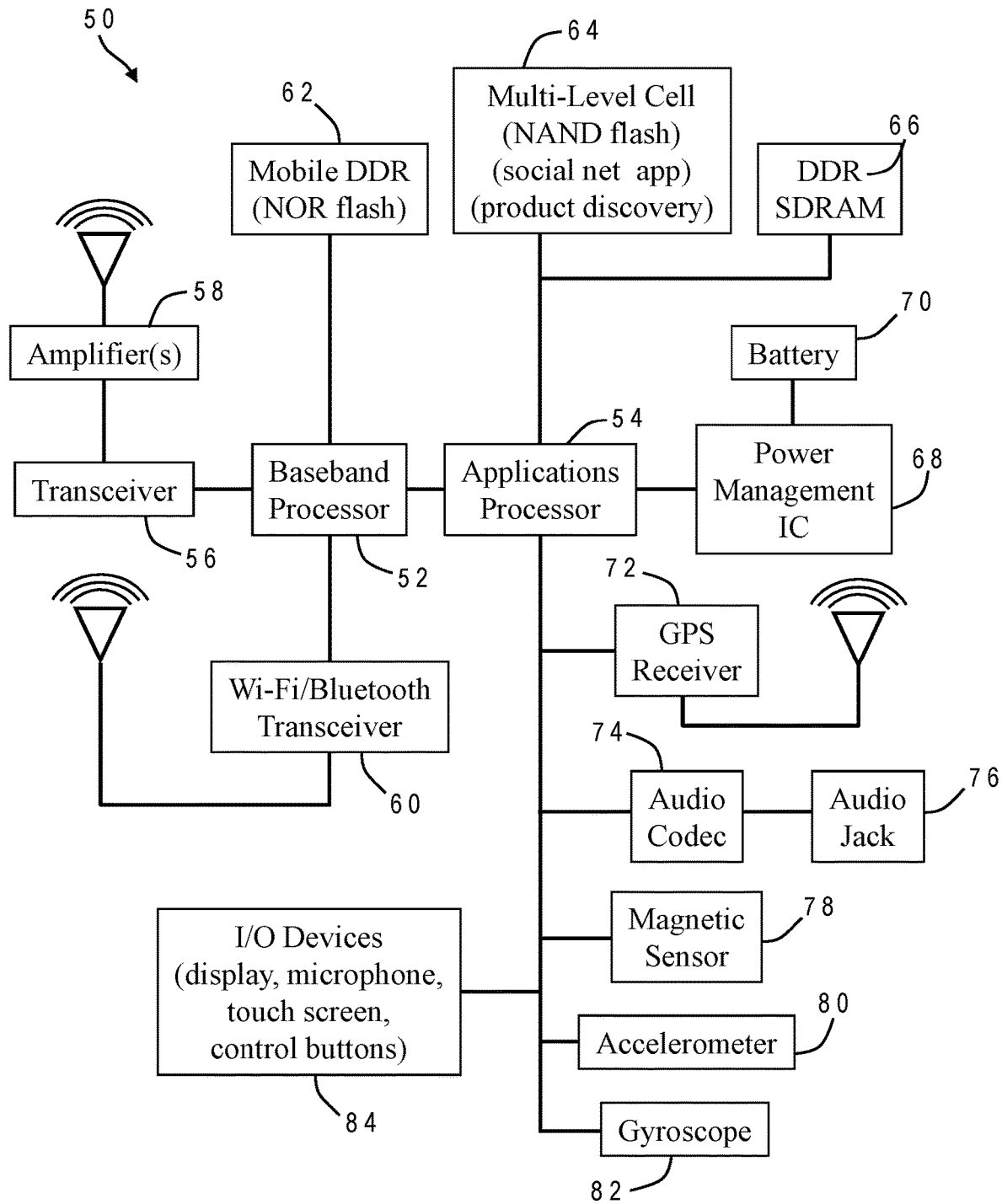
FIG. 2 is a block diagram of a mobile computing device (e.g., smartphone) programmed in accordance with one implementation of the present invention to run a food discovery app that can be used in conjunction with the food product discovery and sharing programs performed by the computer system of FIG. 1.

Referring now to FIG. 2, there is depicted one embodiment 50 of a mobile computing device or smartphone which may be implemented to carry out certain aspects of the present invention by a user. As with computer system 10, alternative embodiments of smartphone 50 may include modifications of the hardware components or their interconnections, or additional components, and other mobile computing devices may be used besides smartphones such as tablets or notebooks, so the depicted example should not be construed as implying any architectural limitations with respect to the present invention. In this example smartphone 50 includes a baseband processor 52 and an applications processor 54. Baseband processor 52 manages most of the radio (wireless communications) functions of smartphone 50, including communication with a wireless service provider (including Internet transmissions) via a transceiver 56 which is connected by one or more power amplifiers 58 to a network antenna. Baseband processor can also control Wi-Fi and Bluetooth transmissions through transceiver 60 connected to a local antenna. Baseband processor 52 uses a dedicated mobile DDR memory (NOR flash) 62.

Baseband processor 52 essentially acts as an input/output (I/O) device with respect to applications processor 54 which executes the software programs (apps) embodying the invention. Those applications may include one or more programs that can also be carried out by computer system 10. Applications processor 54 preferably utilizes multi-level cell memory (NAND flash) 64 and DDR synchronous dynamic random-access memory (SDRAM) 66. In particular, NAND flash 64 may store a social network application and one or more modules relating to the product discovery as discussed herein, particularly with reference to FIGS. 6A and 6B below. Applications processor 54 can interact with a power management integrated circuit 68 to control the power supply (battery) 70. Applications processor 54 can additionally receive inputs from a variety of peripheral devices such as a global positioning satellite (GPS) receiver 72 connected to a GPS antenna, an audio codec 74 which drives an audio (e.g., headphone) jack 76, a magnetic sensor 78 for azimuthal indication, an accelerometer 80 for crash detection and prevention, a 3-axis gyroscope 82 for orientation indication, and user I/O devices 84 (e.g., touch screen/display, microphone and control buttons). Smartphone 50 may include many other hardware features not illustrated, for example, a camera and associated driver circuitry.

When smartphone 50 is first turned on, baseband processor 52 and applications processor 54 may perform various tests such as built-in-self-tests or memory tests on the memory components 62, 64, 66. If the systems pass the tests then each processor begins execution of its primary code, namely, a communications link for baseband processor 52 and an operating system for applications processor 54. Once the network communications have been established by baseband processor 52 and the operating system is loaded by applications processor 54, the user can enter appropriate commands via the touch screen or microphone to load executable code representing embodiments of the present invention for execution by applications processor 54. Any or all of the functionalities of computer system 10 can be incorporated directly into mobile device 50 as computing power and memory storage permit.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include various characteristics, service models, and deployment models.

Characteristics can include, without limitation, on-demand service, broad network access, resource pooling, rapid elasticity, and measured service. On-demand self-service refers to the ability of a cloud consumer to unilaterally provision computing capabilities, such as server time and network storage, as needed automatically without requiring human interaction with the service's provider. Broad network access refers to capabilities available over a network and accessed through standard mechanisms that promote use by heterogeneous thin or thick client platforms (e.g., mobile phones, laptops, and personal digital assistants, etc.). Resource pooling occurs when the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter). Rapid elasticity means that capabilities can be rapidly and elastically provisioned, in some cases automatically, to quickly scale out and rapidly released to quickly scale in. To the consumer, the capabilities available for provisioning often appear to be unlimited and can be purchased in any quantity at any time. Measured service is the ability of a cloud system to automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models can include, without limitation, software as a service, platform as a service, and infrastructure as a service. Software as a service (SaaS) refers to the capability provided to the consumer to use the provider's applications running on a cloud infrastructure. The applications are accessible from various client devices through a thin client interface such as a web browser. The consumer does not manage or control the underlying cloud infrastructure including network, servers, operating systems, storage, or even individual application capabilities, with the possible exception of limited user-specific application configuration settings. Platform as a service (PaaS) refers to the capability provided to the consumer to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations. Infrastructure as a service (IaaS) refers to the capability provided to the consumer to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models can include, without limitation, private cloud, community cloud, public cloud, and hybrid cloud. Private cloud refers to the cloud infrastructure being operated solely for an organization. It may be managed by the organization or a third party and may exist on-premises or off-premises. A community cloud has a cloud infrastructure that is shared by several organizations and supports a specific community that has shared concerns (e.g., mission, security requirements, policy, and compliance considerations). It may be managed by the organizations or a third party and may exist on-premises or off-premises. In a public cloud, the cloud infrastructure is made available to the general public or a large industry group and is owned by an organization selling cloud services. The cloud infrastructure for a hybrid cloud is a composition of two or more clouds (private, community, or public) that remain unique entities but are bound together by standardized or proprietary technology that enables data and application portability (e.g., cloud bursting for load-balancing between clouds).

Figure 3:
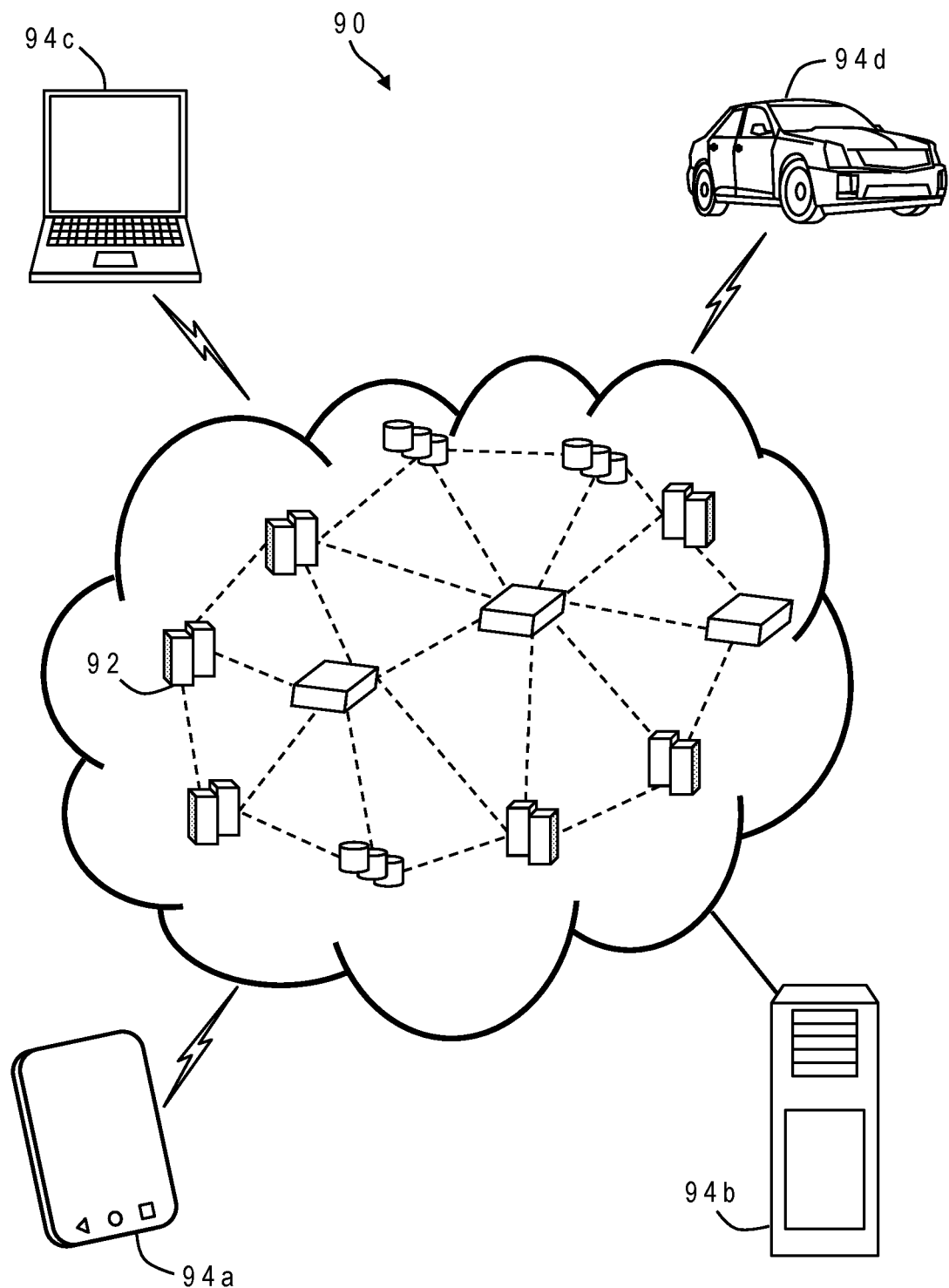
FIG. 3 is a pictorial representation of a cloud computing environment in accordance with one implementation of the present invention.

A cloud computing environment is service oriented with a focus on statelessness, low coupling, modularity, and semantic interoperability. At the heart of cloud computing is an infrastructure that includes a network of interconnected nodes. An illustrative cloud computing environment 90 is depicted in FIG. 3. As shown, cloud computing environment 90 includes one or more cloud computing nodes 92 with which local computing devices used by cloud consumers, such as, for example, personal digital assistant (PDA) or cellular telephone 94*a*, desktop computer 94*b*, laptop computer 94*c*, and/or automobile computer system 94*d* may communicate. Nodes 92 may communicate with one another. They may be grouped (not shown) physically or virtually, in one or more networks, such as private, community, public, or hybrid clouds as described hereinabove, or a combination thereof. This allows cloud computing environment 90 to offer infrastructure, platforms and/or software as services for which a cloud consumer does not need to maintain resources on a local computing device. It is understood that the types of computing devices 94*a*-94*d* shown in FIG. 3 are intended to be illustrative only and that computing nodes 92 and cloud computing environment 90 can communicate with any type of computerized device over any type of network and/or network addressable connection (e.g., using a web browser). In some embodiments one or more of the nodes are computer systems similar to computer system 10 of FIG. 1.

Figure 4:
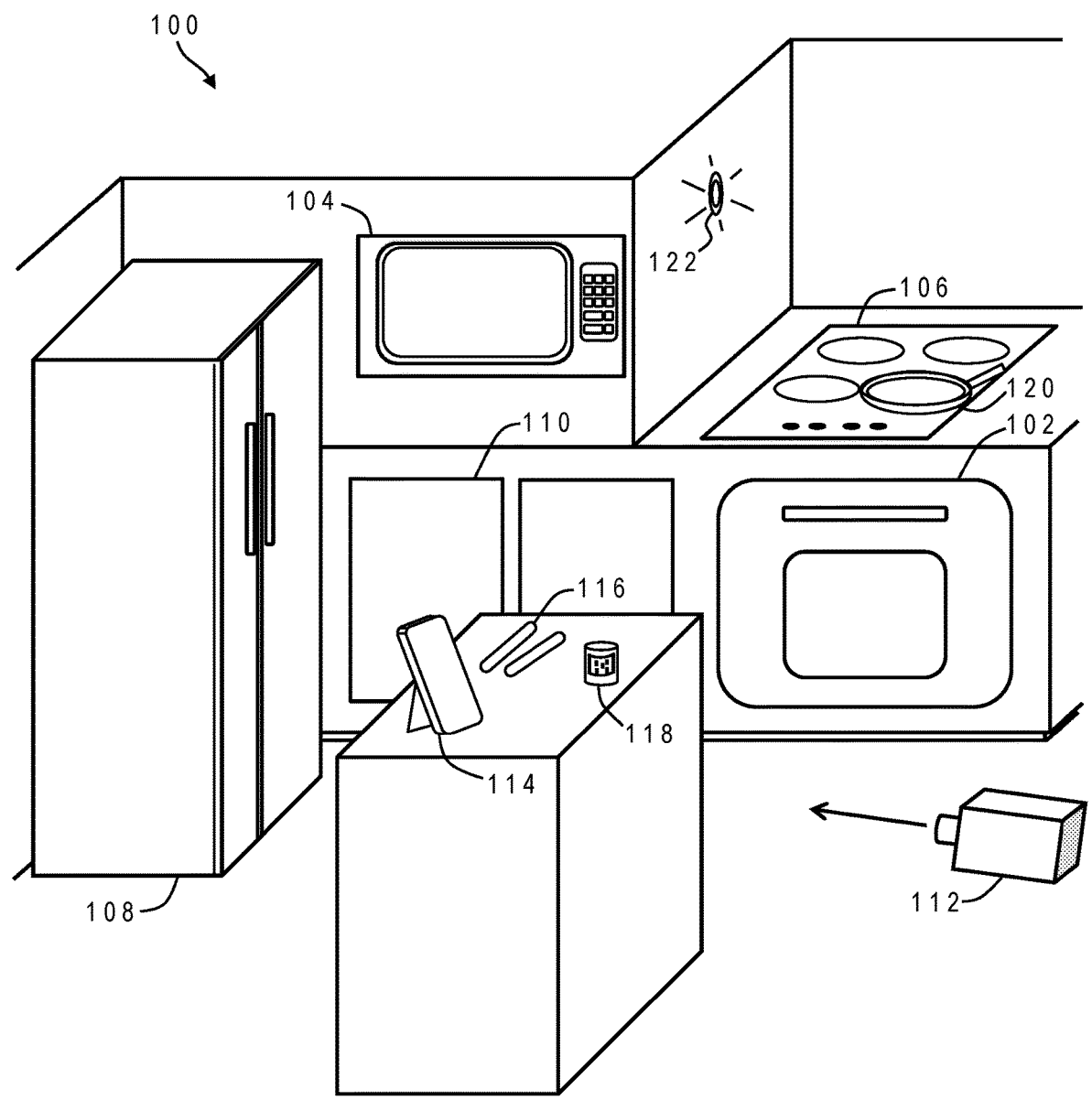
FIG. 4 is a perspective view of a smart kitchen having one or more smart appliances and a camera which can be used with food image recognition to determine food items being prepared in accordance with one implementation of the present invention.

With further reference to FIG. 4, there is depicted one embodiment of a smart kitchen 100 which may be used to carry out portions of the present invention in some implementations. Smart kitchen 100 may have any conventional kitchen features including a variety of appliances, some or all of which can be smart or connected. These appliances can include a traditional (heat transfer) oven 102, a microwave oven 104, a stovetop 106 and a refrigerator 108. Smart kitchen 100 can also have a pantry 110 equipped with a variety of sensors to keep track of current stocks of food supplies. A digital inventory system can keep track of foodstuffs and related items such as those stored in the pantry or refrigerator of the user. Such a system can for example rely on electronic tags (e.g., magnetic strips or RFID markers) attached to the goods. Portions of the digital inventory system may be embodied in various sensors or devices included with or attached to any of the smart appliances.

A camera 112 is positioned to be able to record images from most locations within smart kitchen 100. Camera 112 is intended to be representational in FIG. 4, i.e., it could take many different forms, including a traditional video or still image camera, or a camera that is built into other devices such as a smartphone. Camera 112 and any of the smart appliances can be connected to a computing device such as computer system 10 of FIG. 1 directly via a wi-fi connection or indirectly via a local network or the Internet using appropriate routing devices. A console or other interface 114 can additionally be employed within the smart kitchen setting. Console 114 may be a simple terminal that is connected to another computing device, or a more functional device such as a virtual assistant with connectivity to the various smart appliances and subject to voice commands.

Image recognition software running on the computing device is able to identify various foodstuffs 116 in view of camera 112 and captured as still images. Image recognition can extend to any optical codes that may be printed on cans or other food containers 118 such as quick response (QR) 2-D codes or universal product code (UPC) bar codes. Image recognition can also be used to glean other information from the kitchen environment, for example cooking utensils or implements such as a frying pan 120. Other means may be employed to identify particular food items such as the aforementioned electronic tags that can be read by a local electronic reader in smart kitchen 100. If a microphone is used with camera 112, other information may be inferred from user conversation or dictation. In this manner, the computing device overseeing smart kitchen 100 can make highly accurate predictions as to the particular ingredients being used during food preparation (including food service) as well as the cooking techniques employed in order to carry out product discovery in accordance with the present invention. Additional details can be obtained from image recognition and/or the various smart appliances, such as the quality of an item (e.g., fresh versus canned), size or thickness, the amount of time it was cooked and how (e.g., baked, fried, grilled, etc.), as well as where the food item was purchased. The system can also provide associated information such as caloric content of the meal or other nutritional values.

Figure 5:
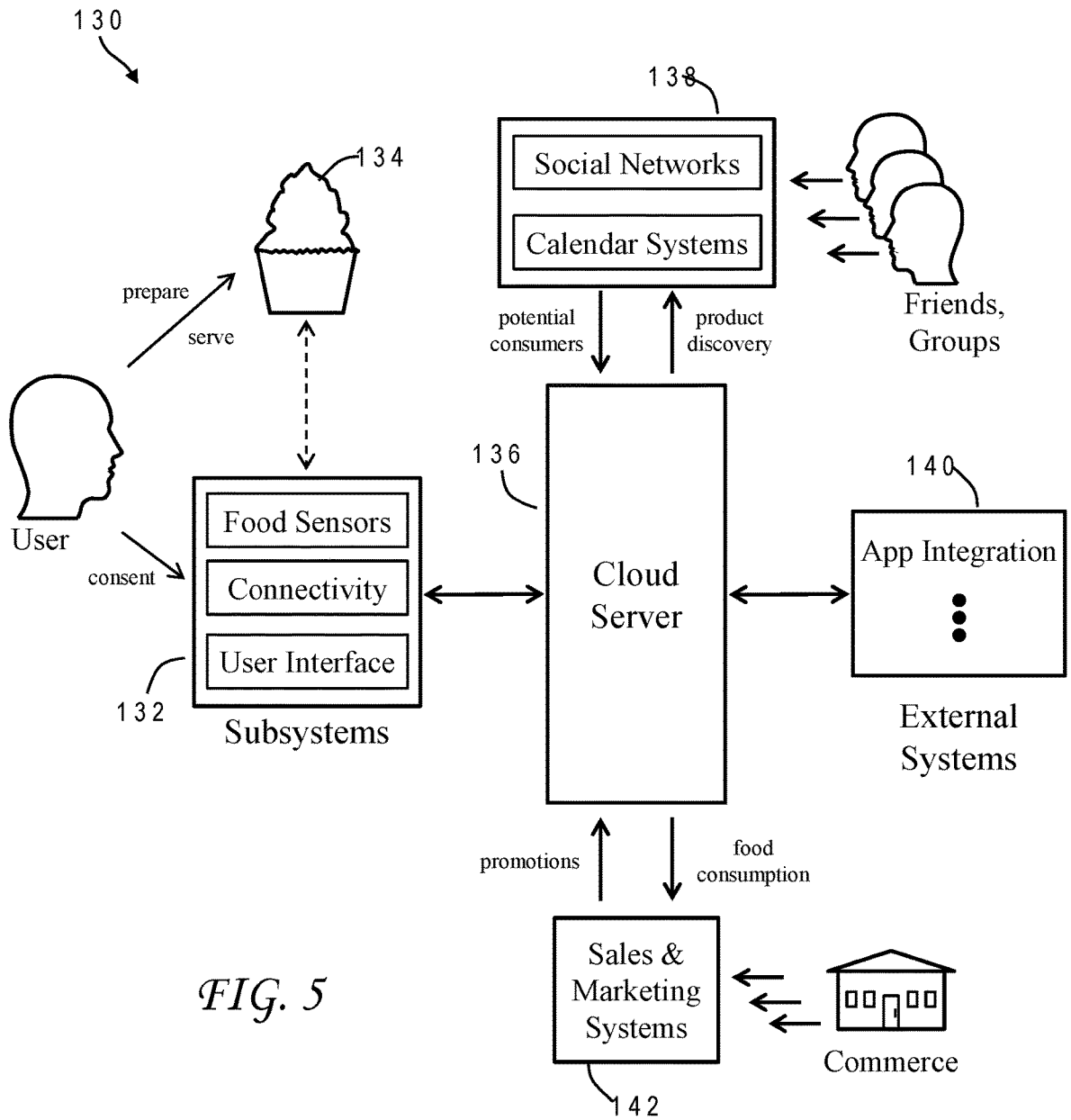
FIG. 5 is a high-level architectural diagram of a product discovery system in accordance with one implementation of the present invention.

FIG. 5 is a high-level architectural diagram showing various aspects of a product discovery system 130 in accordance with one implementation of the present invention. The system preferably includes a user opt-in which allows the user (a client of the cloud computing environment) to consent to the sharing of their food insights including any fine-grained preferences. The consent may be given via an appropriate button, key or prompt in any of the electronic devices or subsystems associated with the system, including the user's smartphone or kitchen computer. Those subsystems 132 may include the food sensors previously described, connectivity devices, and one or more user interfaces, collectively referred to as client devices. As the user prepares and/or serves a food item 134, it comes into range of one or more of the food sensors or scanning devices (e.g., camera 112 or microwave 104). The scanning devices determine the food in scope using a variety of techniques such as image classification, machine-readable codes (e.g., optical or electronic), or other conventional methods. For example, the invention can employ deep learning systems such as a convolution neural network which, given an image of a dish, drink, or ingredient, can determine what the food item is. A convolution neural network is a specific type of feed-forward neural network based on animal visual perception, and so is particularly useful in processing image data. The user can also enter some food information manually.

The food recognition may take place in a computing system local to smart kitchen 100, or remote therefrom, such as on a cloud server 136. Cloud server 136 is connected to any of the devices in smart kitchen 100 via the Internet or other networking service, and can perform product lookup, retrieving food item characteristics and associated information, such as a product name, or list of products used in the dish. Product lookup can be based on archived recipes that have information pertaining to ingredients (including quantities or proportions) or cooking techniques. Cloud server 136 is able to determine possible offers that might be of interest to the user based on the current (and past) food scans and any previously acquired knowledge pertaining to the user. This knowledge can cover specific food products, food ingredients, food combinations (meals), food recipes, or food classes (e.g., kosher, gluten-free, vegan, etc.).

Cloud server 136 can also access other user functions 138 such as social networks or calendar systems to acquire the user's consumer habits as well as information pertaining to other individuals associated with the user, i.e., friends or online groups. Some apps that can provide external user knowledge sources include MyFitnessPal and MapMyRun. For example, either of these apps could provide the knowledge that the user or friend does a lot of strength exercises and therefore would benefit from a protein-rich diet. The user consumption information could additionally include a food intake log to discern that the user consumes a particular food item or type of food item frequently. This information gathering can be facilitated by other external systems 140 such as app integration.

This food consumption information, along with contextual knowledge (the particular user, products involved, specific friends, calendar entries, current events, weather, etc.) can be used to determine what promotions should be offered to the user or others. Knowledge of the promotions can be obtained via sales and marketing systems 142 of various businesses which are also connected to cloud server 136 via the Internet. Sales and marketing systems 142 can obtain food consumption information for the user from cloud server 136 and tailor product offerings based on this information. In a preferred implementation, cloud server 136 determines an optimal time to push an offer to the user. The optimality metric can be based on several factors including the user's purchasing profile, an ideal time for the customer, or timed with the store offering the promotion, or some combination thereof. For example, if a grocery store is currently offering a special for hamburger meat and the user or other individual has shown previous or current interest in hamburgers, the system can wait to push the offer until the individual is shopping at that grocery store. Location information for the user can be provided in a variety of manners, such as global positioning system (GPS) functionality embedded in the user's smartphone along with a monitoring app.

Figure 6A:
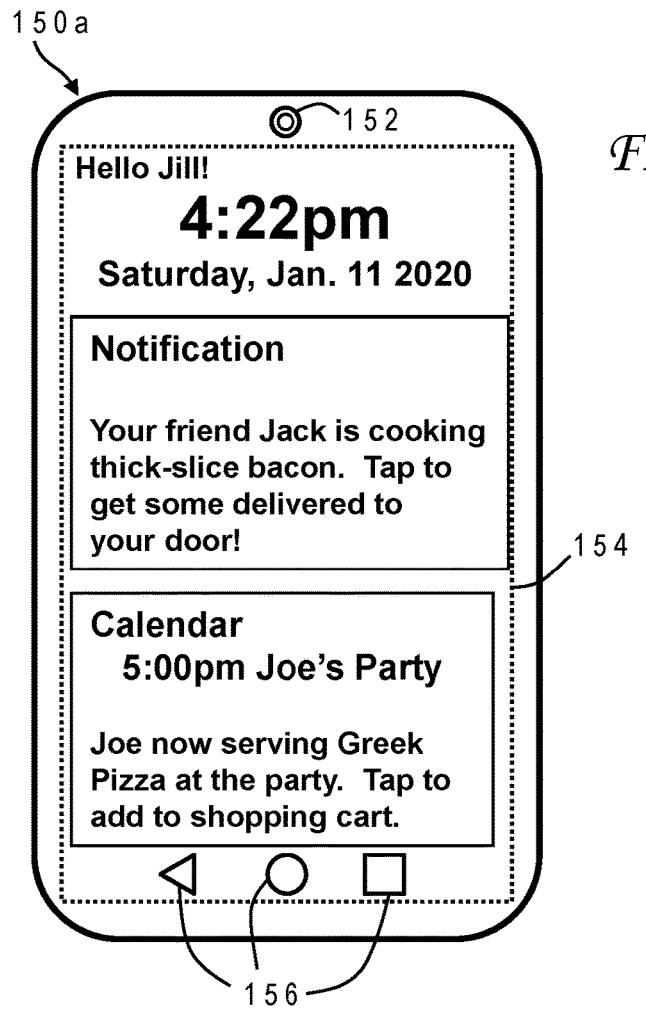
FIGS. 6A and 6B are screenshots of a smartphone showing various notifications that might be generated by the product discovery system in accordance with one implementation of the present invention.
Figure 6B:
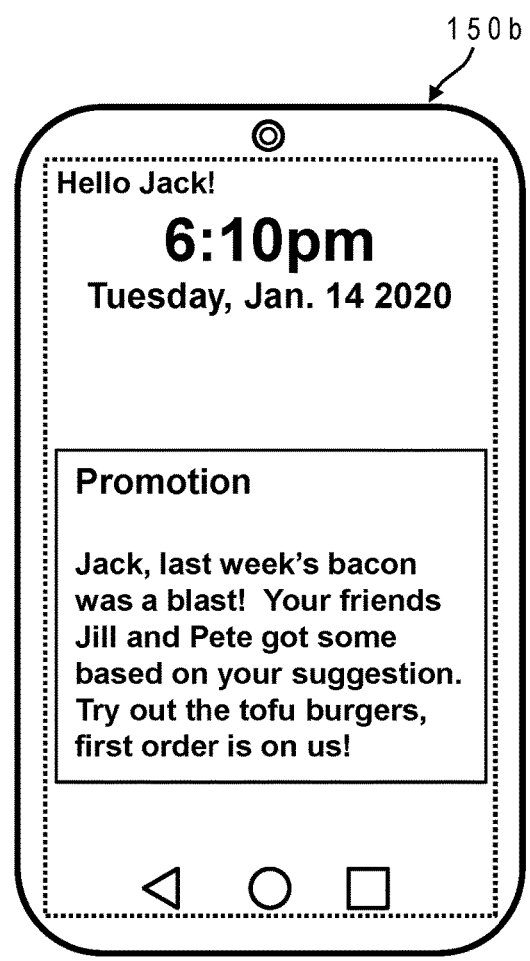

Cloud server 136 can provide these offers or other "calls to action" to friends and acquaintances of the user as well. Offers can be combined with other notifications or calendar entries. Different protocols can be used to provide the offers. Cloud server 136 can "push" responses to a client through protocols such as Web Socket that support bi-directional communication between client and server. Many messaging systems support these protocols in their application programming interfaces. FIGS. 6A and 6B show two different screenshots that might appear on a friend's or user's smartphone 150a, 150b as part of the product discovery of the present invention. Smartphones 150a, 150b may have the same architecture as that seen in FIG. 2, and include a camera 152 and a display screen 154. Display screen 154 may provide various conventional features in addition to the novel features pertinent to the present invention. The conventional features may for example include one or more icons 156 at the bottom of display screen 154 with programmed functionalities. The smartphone can have additional hardware features not shown such as a power on/off button, volume up/down buttons, a microphone and one or more speakers.

The offers pushed by cloud server 136 can vary in format and content according to designer specifications. In an exemplary implementation, the offers are provided with a pop-up notification (for example, about what someone else is preparing or serving at home), as a calendar detail when events are shared by the smartphone's calendar system (for example, showing what is being prepared or served in an upcoming event), or as a merchant promotion (for example, based on referrals). The first two of these types of push offers are seen in FIG. 6A. A notification on the display screen of smartphone 150a informs Jack's friend Jill that "Your friend Jack is cooking thick-slice bacon. Tap to get some delivered to your door!" A calendar entry for later in the day also shown on display screen 154 indicates "Joe now serving Greek Pizza at the party. Tap to add to shopping cart." These display boxes can each have an embedded link to other network sites, e.g., a hypertext transfer protocol (HTTP) link, such that the individual interested in an offer can tap on the box to generate a command that opens a web browser or other smartphone app that connects to a web page or other shopping interface for the company sponsoring the promotion with additional information regarding the offer.

The company can embed appropriate codes in the link to allow the referring user (in this case, Jack) to get credit for any purchase so made. The referring user can get credited with the sale in various ways, such as a reward provided by the sponsoring company. FIG. 6B shows a push offer of the third type mentioned above (merchant promotion) providing an example of such a reward via the user's smartphone 150b. The promotion informs Jack that two of his friends bought some bacon based on his recent referral (i.e., the notification seen in FIG. 6A). The store is rewarding Jack for his friends purchases by offering him a free order of tofu burgers. This promotion can again have an embedded link to facilitate the redemption of the free offer. Another way to credit a referring user is through social media platforms which can aggregate referral purchases to rank the user's social influence (possibly along with other data, such as the number of the user's followers on that platform). Users with higher clout may get more generous offers, such as more free products, since they are deemed to reach a wider audience.

Figure 7:
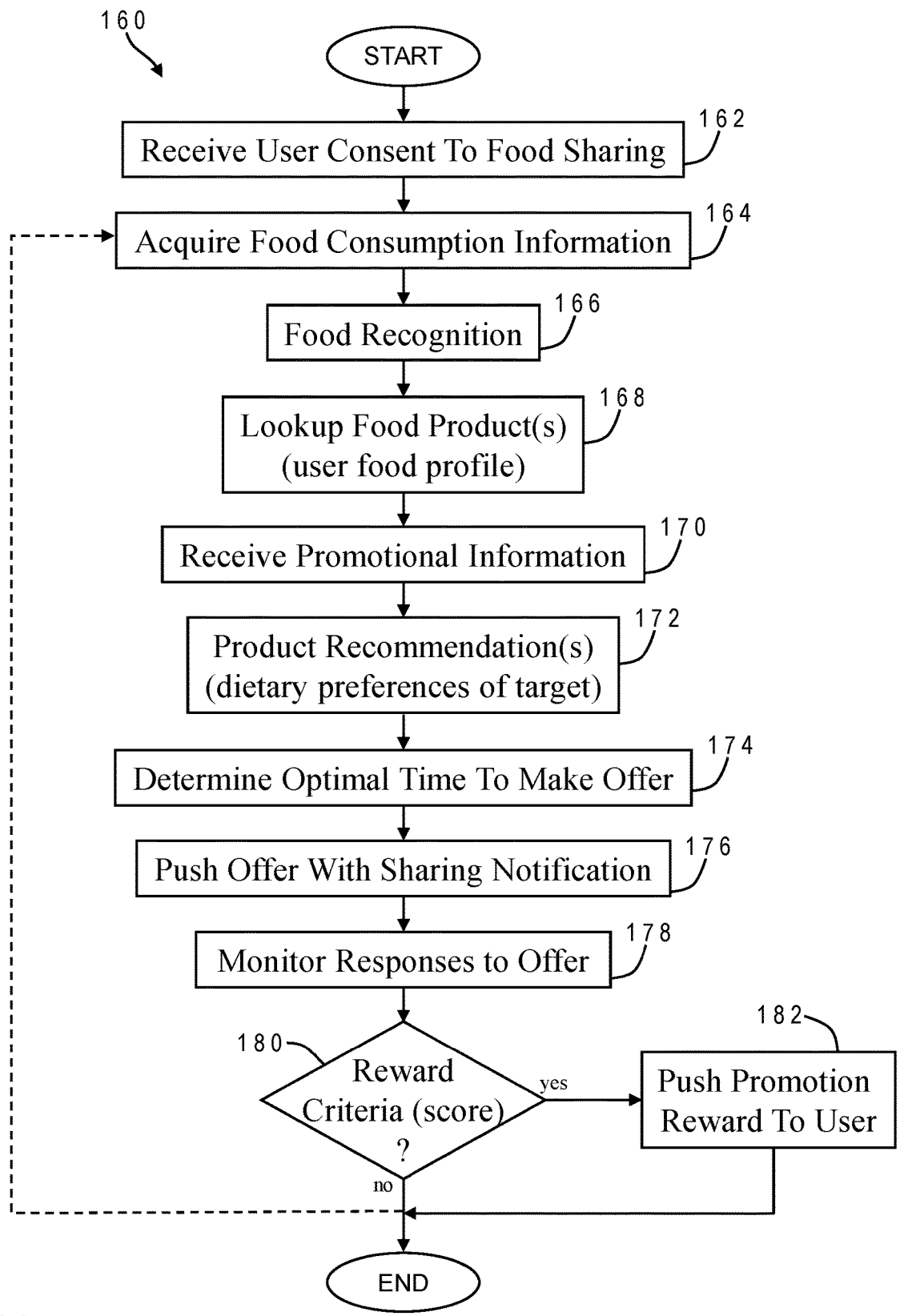
FIG. 7 is a chart illustrating the logical flow for a food product discovery process in accordance with one implementation of the present invention.

The present invention may be further understood with reference to the chart of FIG. 7 which illustrates the logical flow for a food product discovery process 160 in accordance with one implementation of the present invention. Different aspects for effectuating embodiments of the present invention can be practiced by different entities including but not limited to a primary user (e.g., an individual in a kitchen who is making a dish), an intermediary agent, a friend or associate of the user, a cloud computing service, or a marketing service, so the description herein of steps carried out from one particular perspective should not be construed in a limiting sense. Process 160 depicted in FIG. 7 represents one implementation that might be carried out by a cloud computing service such as that embodied in cloud server 136 of FIG. 5. As part of the process, the cloud computing service may receive various communications from smart devices in the connected kitchen or other devices such as smartphones via the Internet or other network connections.

Process 160 begins with receipt by the cloud computing service of the user's opting in to the sharing of their food consumption details 162. This consent may be blanket, i.e., in effect until otherwise canceled, or may be limited to a per-use permission, i.e., with a time limit. The service acquires food consumption information associated with the user by receiving data 164 from the various food sensors in the connected kitchen. If not already performed by a local device in the kitchen, the service can carry out food recognition 166 to identify the various ingredients, food items and cooking techniques. The service performs product lookup 168 using this information along with information gleaned from a food profile for the user. Product lookup may for example determine a particular dish that is being prepared including characteristics of the dish such as flavors (e.g., sweet, sour, bitter, salty, and savory/umami), food types (e.g., vegetarian, keto, paleo, halal, etc.), nutritional classifications (e.g., high protein, low fat, low carb, low salt, etc.) and other characteristics. Characteristics are not necessarily mutually exclusive, i.e., a dish could be both savory and sweet. Product lookup may be accomplished using a cognitive system (i.e., deep learning, or artificial intelligence) trained to identify dishes based on ingredients or preparation styles; the cognitive system can also take into account information from the user profile.

The cloud computing service separately receives promotional information from third-party sales and marketing systems 170. These systems are for a variety of food-related businesses such grocery stores, specialty food stores, appliance and utensil stores, catering companies or restaurants. The cloud computing service can then make product recommendations 172 based on the product lookup for the current food item(s) being prepared. The product recommendations can be targeted to the original user or to individuals associated with the user such as friends on social networks. The cloud computing service can find associated individuals via appropriate APIs programmed into those social networks or through other means such as data mining, or by the user manually designating contacts for the product discovery app. The contact information for an individual can for example include an email address or other means for enabling electronic communications, e.g., a phone number for a device that enables short message service (SMS) texting. The product recommendations can also be based in part on aspects of a food profile for the individual such as flavor preferences or aversions, food restrictions, nutritional requirements, etc. A single food product lookup could result in different offers being made to different individuals based on these dietary preferences.

The service preferably determines an optimal time 174 to deliver the offer to the individual. An ideal time for the individual might be derived from the engagement rate of previous notifications sent to the individual. The offer timing might also depend on store hours, i.e., when a store will be open (it may not be optimal to send the customer a notification if there is a high probability that the customer will view it for the first time while the store is closed). In general there will be a bias toward the earliest time feasible so as to include it with a notification that is still timely regarding the food that was being prepared. The offer is then pushed to the targeted individuals with the product discovery notification 176. The notification may be integrated with other functions of the recipient's smartphone such as adding an invitation for the recipient to join the user for the meal being prepared. The invitation could be part of the smartphone's calendar system or generated via a third-party app. The notification can include ancillary information such as a recipe being used, ingredients, etc.

Any positive responses to the offer are recorded by the service 178 and aggregated for rewards consideration or other rankings such as on social media. Monitoring of the responses can be achieved in any convenient manner, such as including an appropriate code in the embedded link of the notification which identifies both the recipient of the notification and the specific offer that has been accepted. The promotional information received at box 170 can include criteria set by the third-party stores for giving a particular reward. For example, the reward criteria can be a threshold value for an influence score of the user based on referrals obtained via the product discovery system and other influence indicators. If those criteria are met 180 by the positive responses, the reward can be pushed 182 to the user who began process 160 with the food preparation. Process 160 can end at this point or continue iteratively at box 162 at a later time when the user engages in further food preparation.

The present invention in at least some embodiments thereby creates a food preparation and serving system that allows users to share their recipes, ingredients and cooking styles with friends and colleagues, and even make them public to anyone through social networks or events. Eating thus becomes more social, promoting product discovery, and does so in a low-friction manner leveraging smart homes and learning customer habits. When a user sends an e-vite to an extended list of friends the present invention allows the user to share with the invitees what food is being served when they arrive at the home/venue, so they can purchase that product after they experience the dish. The system further provides a data source for merchants and manufacturers which they can use to generate tailored marketing, such as affinity program to reward reorders, referral programs and personalized information.

Although the invention has been described with reference to specific embodiments, this description is not meant to be construed in a limiting sense. Various modifications of the disclosed embodiments, as well as alternative embodiments of the invention, will become apparent to persons skilled in the art upon reference to the description of the invention. Other products besides food could be discovered. For example, a connected kitchen have a smart dishwasher could provide information on what detergents or rinse agents are used, how often, and with what kinds of cleaning cycles. It is therefore contemplated that such modifications can be made without departing from the spirit or scope of the present invention as defined in the appended claims.

What is claimed is:

1. A computer-implemented method of enhancing discovery of food products comprising:

receiving, by a server, an image pertaining to a dish being prepared by a user, the image including an optical code printed on a food container;

identifying the dish, by the server, based, at least in part, on the optical code included in the image;

integrating, by the server, with a social network system to identify contact information pertaining to at least one individual associated with the user;

integrating, by the server, with an electronic sales and marketing system to identify promotional information for a plurality of available sales offers regarding food-related products;

generating, by the server, at least one food product recommendation based on the dish and a particular one of the available sales offers;

sending, by the server, a notification to a computing device of the individual using the contact information, the notification identifying the user, the dish, and the particular available sales offer;

receiving, by the server, a response from the individual indicating acceptance of the particular available sales offer; and responsive to the response, utilizing, by the server, the integration with the social network system to increase an influence score of the user in the social network system, and utilizing, by the server, the integration with the electronic sales and marketing system to credit the user for the acceptance of the particular available sales offer in the electronic sales and marketing system.

2. The computer-implemented method of claim 1 wherein the image is captured by a camera of the user, the camera located in a kitchen setting.

3. The computer-implemented method of claim 1 further comprising receiving, by the server, a food profile of the individual having at least one dietary preference, wherein the food product recommendation is based in part on the dietary preference.

4. The computer-implemented method of claim 1 further comprising receiving, by the server, a food profile of the user, wherein the dish is identified based in part on the food profile of the user.

5. The computer-implemented method of claim 1 further comprising:
establishing, by the server, that the influence score meets reward criteria for a promotion; and
sending, by the server, the promotion to a computing device of the user.

6. The computer-implemented method of claim 1 further comprising determining, by the server, an optimal time to send the notification, wherein said sending occurs at the optimal time.

7. The computer-implemented method of claim 1 further comprising:
receiving, by the server, a command from the individual indicating interest in the particular available sales offer; and
sending, by the server, additional information regarding the particular available sales offer to the computing device of the individual.

8. A computer system comprising:
one or more processors which process program instructions;
a memory device connected to said one or more processors; and
program instructions residing in said memory device for enhancing discovery of food products by:
receiving an image pertaining to a dish being prepared by a user, the image including an optical code printed on a food container,
identifying the dish based, at least in part, on the optical code included in the image,
integrating with a social network system to identify contact information pertaining to at least one individual associated with the user,
integrating with an electronic sales and marketing system to identify promotional information for a plurality of available sales offers regarding food-related products,
generating at least one food product recommendation based on the dish and a particular one of the available sales offers,
sending a notification to a computing device of the individual using the contact information, the notification identifying the user, the dish, and the particular available sales offer,
receiving a response from the individual indicating acceptance of the particular sales offer, and
responsive to the response, utilizing the integration with the social network system to increase an influence score of the user in the social network system, and utilizing the integration with the electronic sales and marketing system to credit the user for the acceptance of the particular available sales offer in the electronic sales and marketing system.

9. The computer system of claim 8 wherein the image is captured by a camera of the user, the camera located in a kitchen setting.

10. The computer system of claim 8 wherein said program instructions further receive a food profile of the individual having at least one dietary preference, the food product recommendation being based in part on the dietary preference.

11. The computer system of claim 8 wherein said program instructions further receive a food profile of the user, wherein the dish is identified based in part on the food profile of the user.

12. The computer system of claim 8 wherein said program instructions further:
establish that the influence score meets reward criteria for a promotion; and
send the promotion to a computing device of the user.

13. The computer system of claim 8 wherein said program instructions further determine an optimal time to send the notification, and send the notification at the optimal time.

14. The computer system of claim 8 wherein said program instructions further:
receive a command from the individual indicating interest in the particular available sales offer; and
responsively send additional information regarding the particular available sales offer to the computing device of the individual.

15. A computer program product comprising:
one or more computer readable storage media; and
program instructions collectively residing in said one or more computer readable storage media for enhancing discovery of food products by:
receiving an image pertaining to a dish being prepared by a user, the image including an optical code printed on a food container,
identifying the dish based, at least in part, on the optical code included in the image,
integrating with a social network system to identify contact information pertaining to at least one individual associated with the user,
integrating with an electronic sales and marketing system to identify promotional information for a plurality of available sales offers regarding food-related products,
generating at least one food product recommendation based on the dish and a particular one of the available sales offers, sending a notification to a computing device of the individual using the contact information, the notification identifying the user, the dish, and the particular available sales offer, receiving a response from the individual indicating acceptance of the particular sales offer, and responsive to the response, utilizing the integration with the social network system to increase an influence score of the user in the social network system, and utilizing the integration with the electronic sales and marketing system to credit the user for the acceptance of the particular available sales offer in the electronic sales and marketing system.

16. The computer program product of claim 15 wherein the image is captured by a camera of the user, the camera located in a kitchen setting.

17. The computer program product of claim 15 wherein said program instructions further receive a food profile of the individual having at least one dietary preference, the food product recommendation being based in part on the dietary preference.

18. The computer program product of claim 15 wherein said program instructions further receive a food profile of the user, wherein the dish is identified based in part on the food profile of the user.

19. The computer program product of claim 15 wherein said program instructions further:

establish that the influence score meets reward criteria for a promotion; and send the promotion to a computing device of the user.

20. The computer program product of claim 15 wherein said program instructions further determine an optimal time to send the notification, and send the notification at the optimal time.

* * * * *